United States Patent [19]

Haber et al.

[11] Patent Number: 4,758,231
[45] Date of Patent: Jul. 19, 1988

[54] SHIELDED SAFETY SYRINGE

[75] Inventors: Terry Haber, Lake Forest; Clark B. Foster, El Toro; William H. Smedley, Lake Elsinore, all of Calif.

[73] Assignee: Habley Medical Technology Corporation, Laguna Hills, Calif.

[21] Appl. No.: 43,042

[22] Filed: Apr. 27, 1987

[51] Int. Cl.⁴ ............................................. A61M 5/32
[52] U.S. Cl. .................................. 604/198; 604/263; 128/763
[58] Field of Search ............... 604/198, 197, 192, 263; 128/763, 764, 765

[56] References Cited

U.S. PATENT DOCUMENTS

| | | | |
|---|---|---|---|
| 3,304,934 | 2/1967 | Bautista | 128/764 X |
| 4,573,976 | 3/1986 | Sampson et al. | 604/198 |
| 4,655,751 | 4/1987 | Harbaugh | 604/198 |
| 4,666,435 | 5/1987 | Braginetz | 604/198 |

Primary Examiner—John D. Yasko
Attorney, Agent, or Firm—Morland C. Fischer

[57] ABSTRACT

A disposable syringe having particular application to vacuum tube phlebotomy and comprising respective inner and outer needle carrying and protective cylinders which are coaxially aligned and axially extensible relative to one another. The inner and outer cylinders may be locked in a retracted position, whereby a hypodermic needle is accessible for drawing blood samples from the patient to an evacuated tube at the inner cylinder. After the last blood sample has been taken, the inner and outer cylinders may be locked in an axially extended position, whereby the hypodermic needle is completely surrounded and shielded by the outer protective cylinder so as to permit the safe handling of the syringe while avoiding an accidental needle strike and the possible spread of a contagious disease.

21 Claims, 10 Drawing Sheets

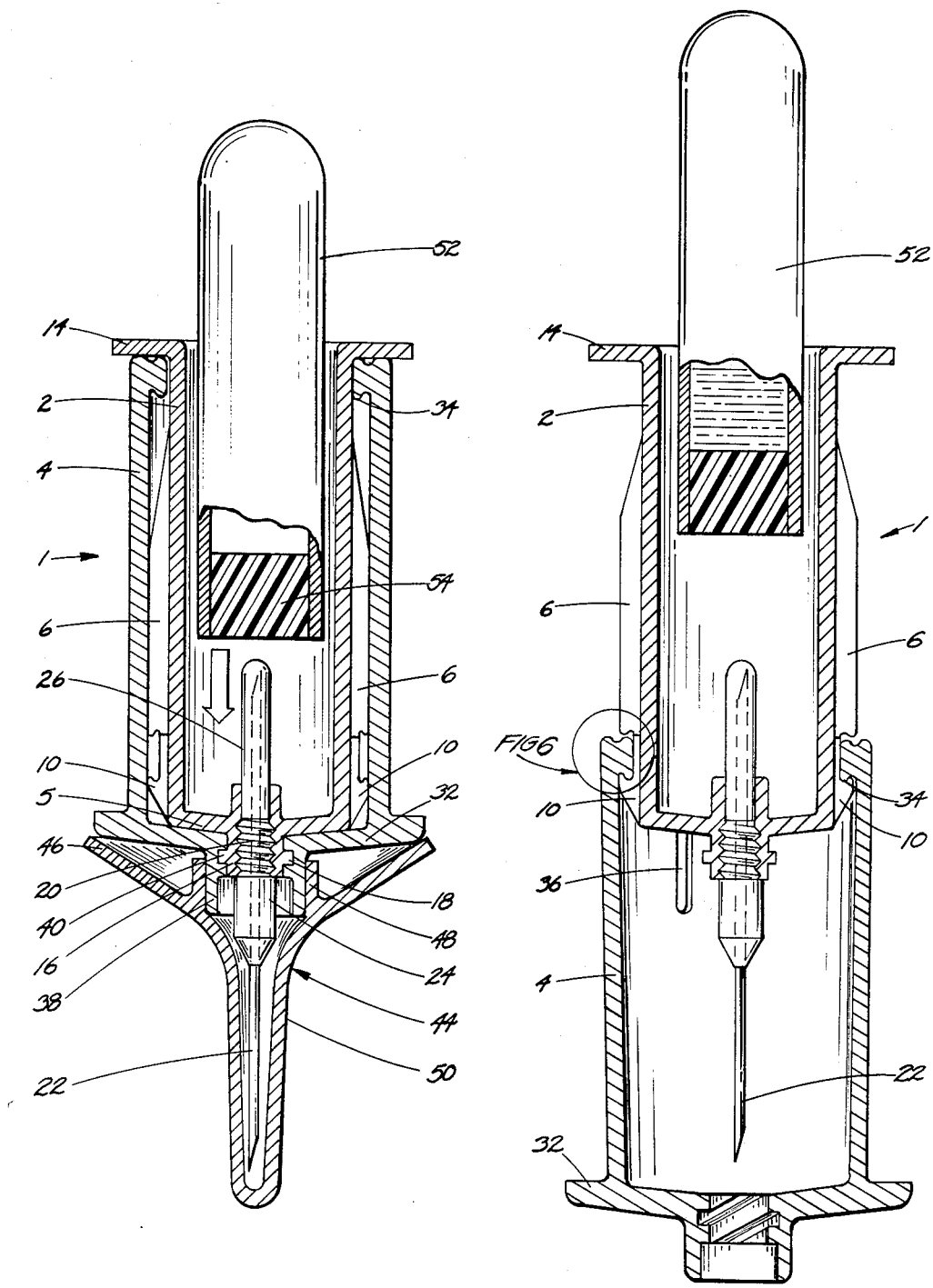

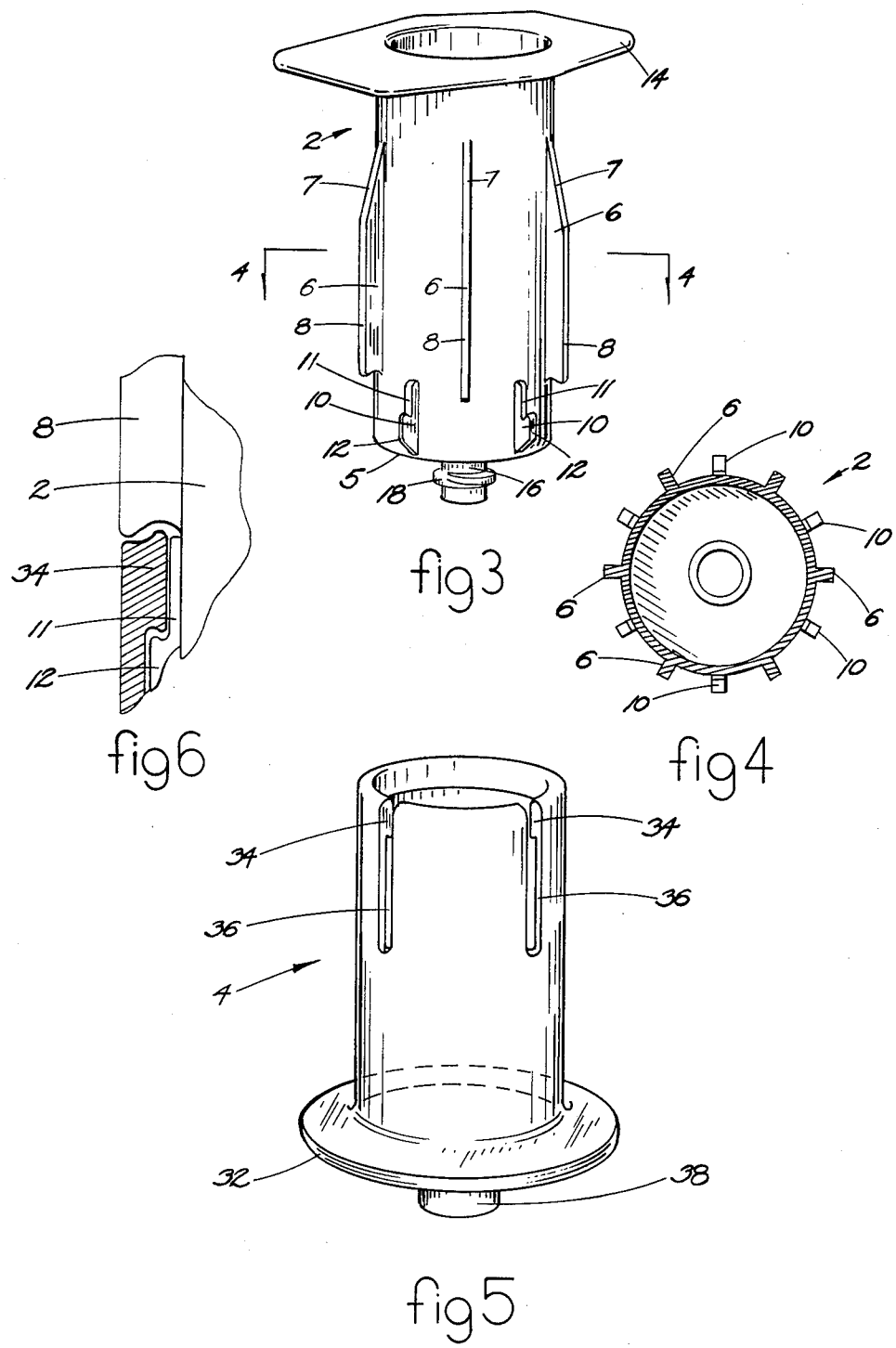

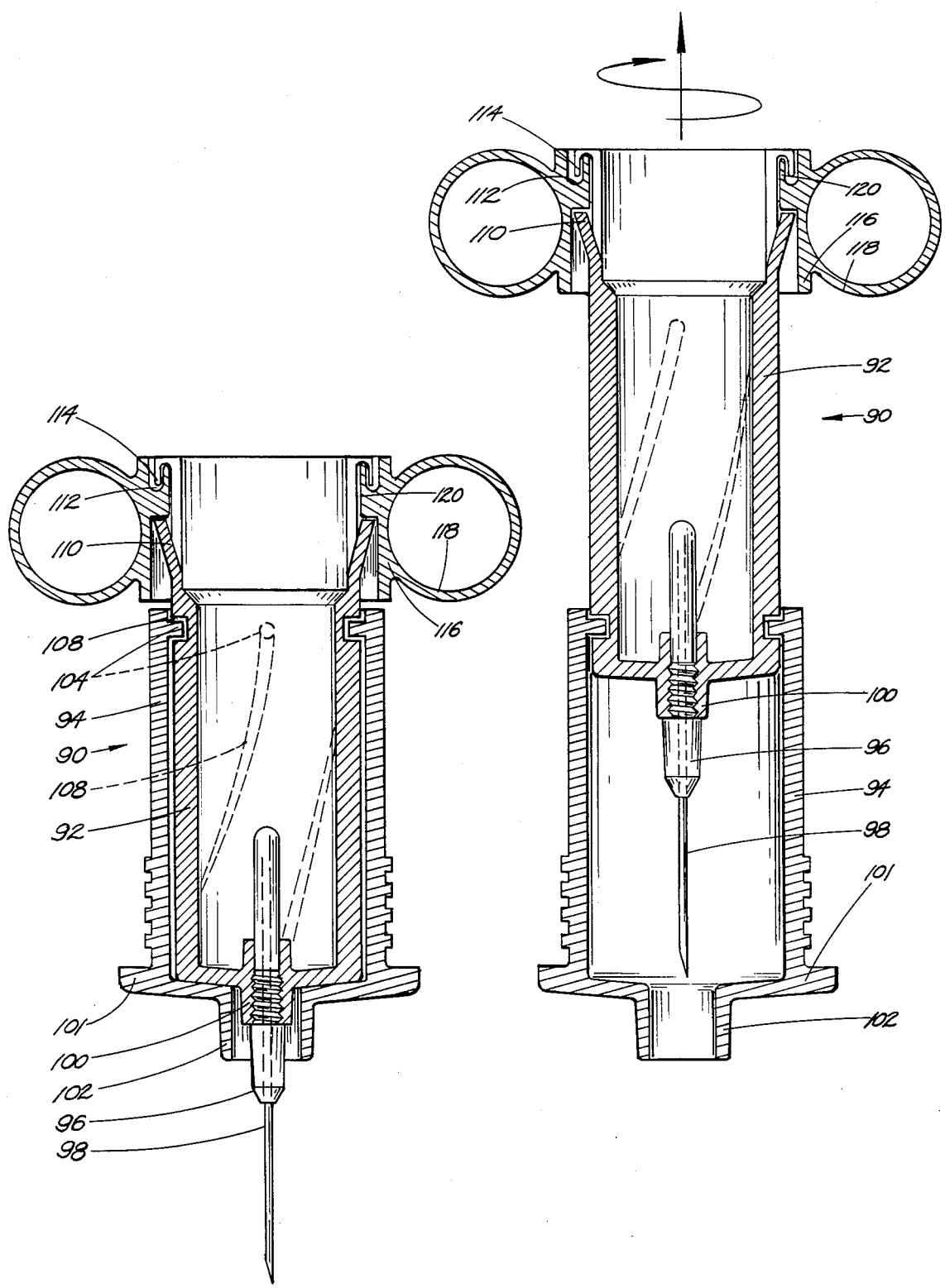

SHIELDED SAFETY SYRINGE

BACKGROUND OF THE INVENTION

1. Field of the Invention

This invention relates to a disposable syringe having particular application to vacuum tube phlebotomy and comprising means by which to shield an associated hypodermic needle to reduce the possibility of an accidental, and possibly life threatening, needle strike and the spread of contagious disease.

2. Prior Art

Hypodermic syringes are used for a variety of purposes. By way of a first example, the syringe may be used for vacuum tube phlebotomy, where samples of the patient's blood are successively drawn into respective evacuated tubes by way of a double ended hypodermic needle. In a second example, the syringe may be used to expulse fluid medication to a patient by way of a single ended hypodermic needle and a conventional injection procedure. In either example, the syringe may be used to treat a patient having a communicable disease. Prior to disposal of the syringe, the hypodermic needle thereof is sometimes broken to prevent reuse. Health care workers are especially susceptible to accidental and potentially infectious needle strikes due to the careless handling or breaking of the needle and disposing of the syringe after use. The resulting mini-accidents caused by an accidental needle strike typically require a blood test for such diseases as AIDS and hepatitis. The corresponding cost and inefficiency of testing health care workers who have received an inadvertent needle strike result in considerable waste, which may particularly damaging to a health care facility which is striving for economy.

The following U.S. patents provide examples of syringes having a hypodermic needle which may be shielded after use to prevent an accidental needle strike:

U.S. Pat. No. 2,571,653, Oct. 16, 1951;
U.S. Pat. No. 4,356,822, Nov. 2, 1982;
U.S. Pat. No. 4,425,120, Jan. 10, 1984;
U.S. Pat. No. 4,631,057, Dec. 23, 1986.

SUMMARY OF THE INVENTION

In general terms, a disposable syringe is disclosed having particular application to vacuum tube phlebotomy. The syringe comprises an inner hypodermic needle carrying syringe and an outer protective sleeve which are coaxially aligned and axially extensible relative to one another. That is, the inner cylinder and outer sleeve may be locked in a retracted position, whereby the needle is accessible for drawing blood from the patient to an evacuated phlebotomy tube at the inner cylinder. The inner cylinder and outer sleeve may also be locked in an axially extended position, whereby the needle is completely surrounded and shielded by the outer sleeve to assure safe handling of the syringe while avoiding an accidental needle strike and the possible spread of a contagious disease.

In a first embodiment of the invention, a plurality of longitudinally extending ribs and stops extend around the exterior of the inner cylinder. The stops are spaced distally from and interspersed between successive pairs of ribs. A lip is formed around the proximal end of the outer sleeve. The outer sleeve is advanced axially relative to the inner cylinder from the retracted to the extended position, such that the lip of the outer sleeve rides up and over the fins for receipt within the spaces between the ribs and stops. A self-locking feature is established when the lip of the outer cylinder is received between the ribs and stops of the inner cylinder to prevent the detachment of the outer sleeve from the inner cylinder and a return of the outer sleeve to the retracted position.

In a second embodiment, proximal and distal grooves are formed in and around the periphery of the inner cylinder. Each of a pair of spring-like locking members includes an oppositely extending arm and leg which are hingedly connected to a respective pivot at the proximal end of the outer sleeve. The inner cylinder and outer sleeve are locked in the retracted position when the legs of the locking members are received in the proximal groove of the inner cylinder. Equal and opposite compressive forces are applied to the arms of the locking members to cause the legs thereof to rotate out of the proximal groove in the inner cylinder. The outer sleeve is then axially advanced relative to the inner cylinder from the retracted to the extended position. A self-locking feature is established when the normal bias of the spring-like locking members automatically rotates the respective legs thereof into the distal groove of the inner cylinder to prevent the detachment of the outer sleeve from the inner cylinder.

In a third embodiment, a plurality of longitudinally aligned, spiraling grooves are formed in the inner cylinder. A corresponding plurality of raised bumps extend radially inward from the outer sleeve. The inner cylinder and outer sleeve are locked in the retracted position when the bumps of the outer sleeve are received at the proximal ends of respective grooves in the inner cylinder. The inner cylinder is axially advanced relative to the outer sleeve from the retracted to the extended position, such that the bumps of the outer sleeve ride through the spiraling grooves of the inner cylinder to cause the inner cylinder to rotate. A self-locking feature is established when the bumps of the outer sleeve are received at the distal ends of the spiraling grooves to prevent the detachment of the inner cylinder from the outer sleeve.

In a fourth embodiment, a first and second series of relatively short ramps extend outwardly from the periphery of the inner cylinder. A first of the series of ramps are spaced proximally from and interspersed between successive pairs of the second series of ramps. A rim extends inwardly from the proximal end of the outer sleeve. The outer sleeve is advanced axially relative to the inner cylinder from the retracted to the extended position, such that the rim of the outer sleeve rides up and across the first series of ramps for receipt within an annular gap established between the first and second series of ramps. A self-locking feature is established when the rim of the outer cylinder is received with said gap to prevent the detachment of the outer sleeve from the inner cylinder and a return of the outer sleeve to the retracted position.

In a fifth embodiment, a first and second series of relatively short ramps project outwardly and in different directions from the repsective intersections of adjacent sidewall which define a hexagonal inner cylinder. A first of the series of ramps are spaced proximally from the second series of ramps. A rim extends inwardly from the proximal end of the outer sleeve. The outer sleeve is advanced axially relative to the inner cylinder from the retracted to the extended position, such that the rim of the outer sleeve rides up and across the first series of ramps for receipt within an annular gap established between the first and second series of ramps. A self-locking feature is established when the rim of the outer cylinder is received within said gap to prevent the detachment of the outer sleeve from the inner cylinder and a return of the outer sleeve to the retracted position.

BRIEF DESCRIPTION OF THE DRAWINGS

FIG. 1 shows a cross-section of a shielded syringe according to a first embodiment of the invention having an inner needle carrying cylinder and an outer protective sleeve locked in a retracted position relative to one another;

FIG. 2 shows the cross-section of the syringe with the inner cylinder and outer sleeve axially advanced relative to one another to the extended position;

FIG. 3 is an isometric illustration of the inner cylinder;

FIG. 4 is a cross-section taken along lines 4—4 of FIG. 3;

FIG. 5 is an isometric illustration of the outer sleeve;

FIG. 6 is an enlarged detail taken from FIG. 2;

FIG. 10 shows a cross-section of the shielded syringe according to a third embodiment of the invention having an inner needle carrying cylinder and an outer protective sleeve locked in a retracted position relative to one another;

FIG. 11 shows the cross-section of the syringe of the third embodiment with the inner cylinder and outer sleeve axially advanced relative to one another to the extended position;

DESCRIPTION OF THE PREFERRED EMBODIMENT

Figures 7, 8:
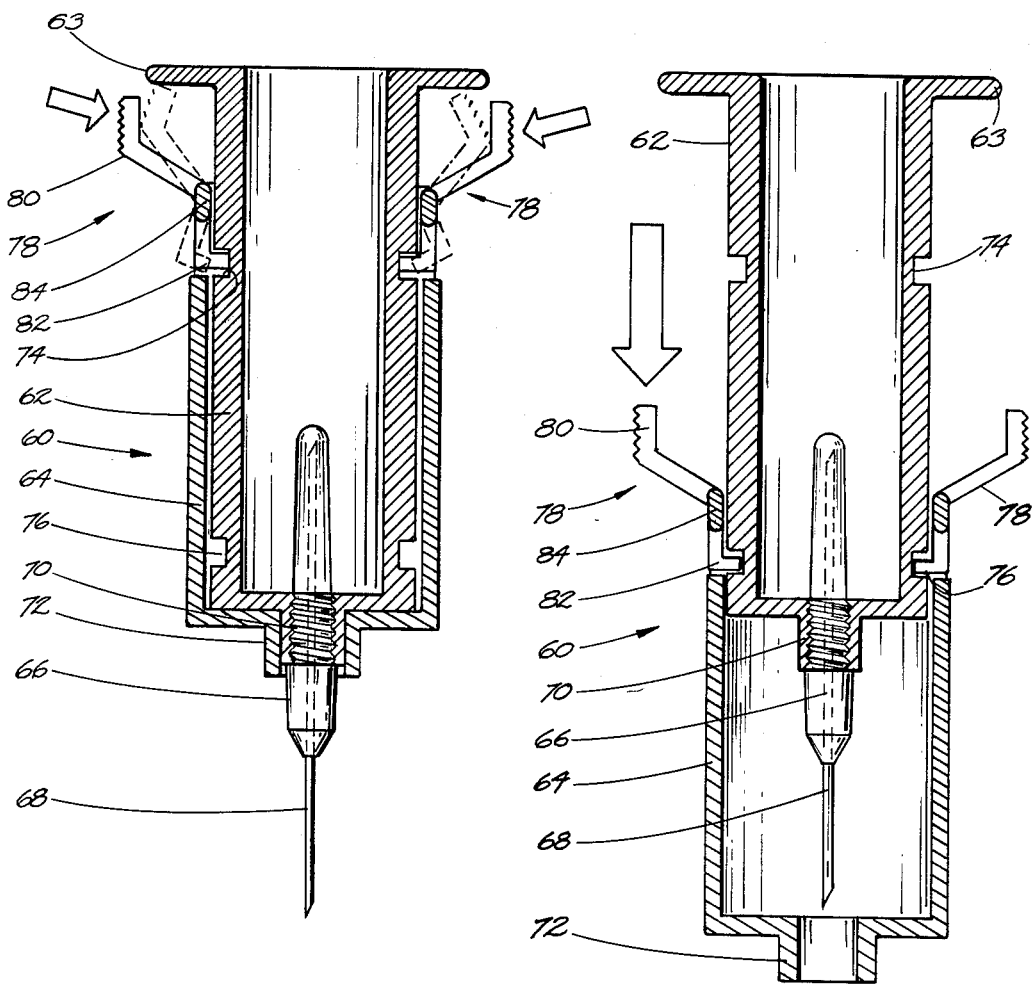
FIG. 7 shows a cross-section of a shielded syringe according to a second embodiment of the invention having an inner needle carrying cylinder and an outer protective sleeve locked in a retracted position relative to one another.
FIG. 8 shows a cross-section of the syringe of the second embodiment with the inner cylinder and outer sleeve axially advanced relative to one another to the extended position.

A first embodiment of the present invention for a shielded safety syringe is best described while referring to FIGS. 1-6 the drawings. Although the syringes illustrated in the drawings hereof have particular application to vacuum tube phlebotomy (i.e. to successively drawing one or more samples of blood into respective vacuum tubes), it is to be expressly understood that the safety features of this invention are also applicable to a syringe in which a fluid medication is expulsed into a recipient by means of a conventional injection procedure. Referring initially to FIG. 1, there is shown a hypodermic syringe assembly 1 comprising an inner syringe barrel or cylinder 2 and a cylindrical outer protective sleeve 4. The inner cylinder 2 and outer sleeve 4 are coaxially aligned and axially extensible relative to one another, such that the outer sleeve 4 is adapted for movement between a retracted position (of FIG. 1) and an axially extended position (of FIG. 2).

Details of the inner syringe cylinder 2 are disclosed while referring concurrently to FIGS. 1, 3 and 4 of the drawings. Inner cylinder 2 is preferably formed from a clear plastic material and has an open proximal end and a wall 5 which defines a substantially closed distal end. Coextensively formed with and projecting radially outward from the inner cylinder 2 are a series of elongated ribs 6. Ribs 6 extend longitudinally and in spaced, parallel alignment with one another around the exterior of inner cylinder 2. Each rib 6 includes a proximally oriented ramp portion 7 and a contiguous, distally oriented step portion 8 (best shown in FIG. 3).

Also coextensively formed with and projecting radially outward from the inner cylinder 2 are a series of relatively short fins 10. Fins 10 are arranged in spaced, parallel alignment with one another around the distal end of inner cylinder 2. However, and as is best shown in FIGS. 3 and 4 of the drawings, the fins 10 are interspersed between respective pairs of ribs 6. Each fin 10 includes a proximally oriented seat portion 11 and a contiguous, upwardly extending and distally oriented stop portion 12. As best shown in FIG. 3, the seat portions 11 of fins 10 lie below and between the step portions 8 of ribs 6 and the stop portions 12 of fins 10, for a purpose which will be described in greater detail hereinafter.

Extending around the open proximal end of inner cylinder 2 is a flange 14. Projecting outwardly from the distal end wall 5 of inner cylinder 2 is a neck 16. A screw thread 18 is formed around the outer periphery of neck 16 to be mated to a corresponding screw thread formed in the distal end of outer sleeve 4 in order to interconnect the distal ends of inner cylinder 2 and outer sleeve 4 when the outer sleeve is moved to a retracted position relative to the inner cylinder and a hypodermic needle 22 is to be made accessible.

A hole is formed through the neck 16 to define a distal bore which communicates with the interior of inner cylinder 2. The distal bore is threaded to receive therewithin a correspondingly threaded end 20 of a hub 24 which carries a conventional double ended needle 22. The needle carrying hub 24 is removably secured to the distal bore within neck 16, so that a first end of the needle 22 projects into the inner cylinder 2 and the opposite end thereof projects outwardly from the inner cylinder. A soft rubber sheath 26 covers the end of the needle 22 which projects into the inner cylinder 2.

Details of the outer protective sleeve 4 are now described while referring concurrently to FIGS. 1 and 6 of the drawings. Outer sleeve 4 is preferably formed from a resilient plastic material and has an open proximal end and a flanged wall 32 which defines a substantially closed distal end. An annular lip 34 extends around the interior of the open proximal end. A plurality of parallel aligned, longitudinally extending slots 36 (best shown in FIG. 6) are formed through outer sleeve 4 from the open proximal end thereof. The slots 36 maximize the flexibility of the proximal end of sleeve 4 when such end is snapped into locking engagement with the inner cylinder 2, in a manner that will soon be disclosed when referring to FIG. 2.

Projecting outwardly from the distal end wall 32 of outer sleeve 4 is a hollow neck 38. The neck 38 of outer sleeve 4 is sized to accommodate the neck 16 of inner cylinder 2 therewithin. A screw thread 40 is formed around the inside periphery of neck 38 to be mated, as previously indicated, to the corresponding screw thread 18 formed around the neck 16 (best illustrated in FIG. 1) when the outer sleeve 4 is located in the retracted position relative to inner cylinder 2 and the distal ends of inner cylinder 2 and outer sleeve 4 are interconnected at their respective necks 16 and 38 to permit access to needle 22.

A flared sheath 44 is also disclosed by which to avoid an accidental needle strike as a consequence of a careless handling of the syringe 1 with the needle 22 exposed. As is best shown in FIG. 1, the protective sheath 44 has a conical base 46 which is sized to surround the flanged distal end wall 32 of outer sleeve 4. An annular receptacle 48 extends from the conical base 46 for receiving therewithin the neck 38 of outer sleeve 4 in order to removably attach the sheath 44 to the outer sleeve (i.e. at the distal end of syringe 1). Coextensively formed with and projecting from the conical base 46 of sheath 44 is a tapered nose portion 50 in which the needle 22 is to be located. That is to say, the protective sheath 44 is attached to the distal end of syringe 1 when the outer sleeve 4 is located in the retracted position relative to inner cylinder 2, such that needle 22 is exposed. By virtue of the conical base 46 of flared sheath 44, a relatively large target area and guide are provided by which to reliably and automatically align the needle 22 for receipt within nose portion 50. In this fashion, the protective sheath 44 and the wide target area provided by the conical base 46 thereof advantageously enable the syringe user to accurately and safely locate a hypodermic needle within a shielded, protective housing while avoiding the possibility of inadvertently striking himself, a problem which is inherent with conventional narrow bodied needle caps.

The operation of the syringe 1 is best disclosed when referring concurrently to FIGS. 1-6 of the drawings. In FIG. 1, the outer sleeve 4 is located in the retracted position relative to inner cylinder 2, and the lip 34 of outer sleeve 4 is disposed proximally of the ribs 6 which extend along inner cylinder 2. The protective sheath 44 is then removed from the syringe 1 to make the exposed needle 22 accessible for penetrating the skin of the patient. A conventional, evacuated phlebotomy tube 52 having a rubber stopper 54 located in the open end thereof is moved through the open proximal end of inner cylinder 2. The tube 52 is then moved into contact with the needle 22 at the interior of cylinder 2, such that the needle penetrates the rubber stopper 54. A blood sample is automatically suctioned, in a well-known manner, from the patient to fill the tube 52 via needle 22.

When the last blood sample has been taken, the hypodermic needle 22 is withdarwn from the patient. In order to prevent an accidental needle strike and the possible spread of contagious disease from a contaminated needle, the previously connected distal ends of inner cylinder 2 and outer sleeve 4 are rotated out of engagement with one another, and the outer sleeve 4 is moved to an axially extended position relative to inner cylinder 2 (best represented in FIG. 2) by grasping the inner cylinder 2 at flange 14 and outer cylinder 4 below flanged end wall 32 and sliding the sleeve 4 over the cylinder 2. More particularly, the displacement of outer cylinder 4 causes a corresponding movement of the annular lip 34 up the ramps 7 and over the steps 8 of ribs 6 (best shown in FIG. 3). Because of its resilient nature, the lip 34 (which is separated into flexible lip sections by the longitudinally extending slots 36) will be rotated outwardly and, thereby, stressed as the lip 34 rides up the ramp portions 7 of ribs 6. The continued axial advancement of outer sleeve 4 relative to inner cylinder 2 will cause the lip 34 to be snapped onto the recessed seats 11 of fins 10 between the stops 12 thereof and the steps 8 of fins 6 (best shown in FIG. 6).

Thus, a positive, self-locking feature is established, because the lip 34 of outer sleeve 4 is securely and permanently retained below and between the elevated steps 8 and stops 12, whereby to prevent both the continued axial advancement of outer sleeve 4 past inner cylinder 2 as well as a return of the outer sleeve to the retracted position. What is more, because the seats 11 of fins 10 extend above the exterior surface of inner cylinder 2, the lip 34 of outer sleeve 4 will not return to a totally relaxed condition, but will remain slightly stressed, when received upon the seats 11. The corresponding compressive force exerted by the flexible lip 34 of sleeve 4 will prevent the removal of lip 34 from the recessed seats 11 and the detachment of the outer sleeve 4 from the inner cylinder 2.

By virtue of the foregoing, a disposal cartridge (of FIG. 2) is created having the inner cylinder 2 and outer sleeve 4 locked in an axially extended position relative to one another with the hypodermic needle 2 surrounded, completely shielded, and rendered irretrievable therewithin so as to permit the safe handling of syringe 1 while avoiding an accidental needle strike. Accordingly, the specimen tube 52 may be detached from needle 22 and removed through the open proximal end of inner cylinder 2. However, because of the permanent nature of the interlocking engagement between inner cylinder 2 and outer sleeve 4, the syringe 1 cannot be reused. Moreover, the used syringe is in a condition to permit safe disposal without requiring the removal or handling of the needle 22 as has heretofor been necessitated as a consequence of many conventional syringe assemblies.

Figure 9:
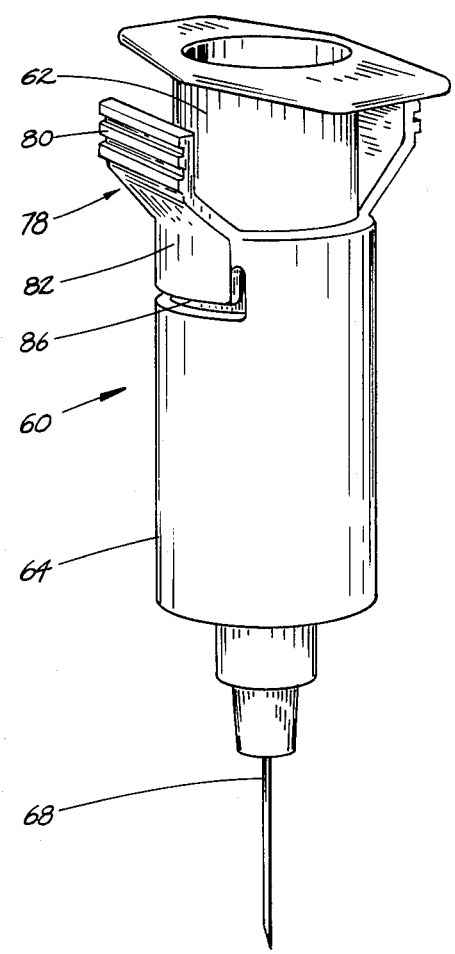
FIG. 9 is an isometric illustration of the syringe according to the second embodiment.

FIGS. 7-9 of the drawings show a second embodiment of the present invention for a shielded safety syringe. Like the syringe 1 of FIGS. 1-6, the syringe 60 of FIGS. 7-9 includes an inner syringe barrel or cylinder 62 and a cylindrical outer protective sleeve 64. The proximal ends of cylinder 62 and sleeve 64 are open, and the distal ends thereof are substantially closed. The inner cylinder 62 and outer sleeve 64 are coaxially aligned and axially extensible relative to one another, such that outer sleeve 64 is adapted for movement between a retracted position (of FIG. 7) to an axially extended position (of FIG. 8).

Also like the syringe 1, syringe 60 includes a screw threaded hub 66 which caries a double ended hypodermic needle 68. The needle carrying hub 68 is retained within a distal bore formed through a neck 70 which extends from the distal end wall of inner cylinder 62, whereby one end of needle 68 projects outwardly from the inner cylinder 62, and the opposite end projects into the cylinder 62 for communication with an evacuated phlebotomy tube (not shown). The outer sleeve 64 includes a hollow neck 72 which is sized to accommodate the neck 70 of inner cylinder 62 so that a tight friction fit is formed therebetween when the outer sleeve 64 is located at the retracted position relative to inner cylinder 62. Accordingly, the distal ends of inner cylinder 62 and outer cylinder 64 can be temporarily joined at their respective necks 70 and 72 to retain syringe 60 in the retracted position and thereby provide access to needle 68 (best shown in FIG. 7).

The inner cylinder 62 includes a pair of grooves 74 and 76 extending around the periphery thereof. A first groove 74 is located below the open proximal end of cylinder 62, and the second groove 76 is located above the distal end wall thereof.

The outer sleeve 64 includes a pair of oppositely disposed, spring-like locking members 78 by which to secure the outer protective sleeve 64 in either of the retracted or axially extended positions relative to inner cylinder 62. More particularly, each locking member 78 includes an arm 80 and a leg 82 which are coextensively formed with and hingedly connected to the outer sleeve 64 at a joint 84 located at the periphery of the open proximal end of sleeve 64. As will soon be explained, the arms and legs 80 and 82 of locking members 78 are adapted to rotate around their respective joints 84 to form what is known in the art as a living hinge assembly. To accommodate the rotation of the legs 82 of locking members 78 towards inner cylinder 62, laterally extending slots (best shown in FIG. 9) are formed through the outer sleeve 64 below the joints 84.

The operation of the syringe 60 is best described while continuing to refer to FIGS. 7-9 of the drawings. In FIG. 7, the outer sleeve 64 is located at the retracted position relative to inner cylinder 62 and the legs 82 of locking members 78 are shown in their normal bias extending through the slots 86 (of FIG. 3) in outer sleeve 64 for receipt by the proximal groove 74 of inner cylinder 62. With the legs 82 of locking members 78 located in grooves 74, the arms 80 are radially spaced from the outer sleeve 64. The hypodermic needle 68 is now exposed for penetrating the skin of the patient, so that a phlebotomy tube (not shown) may be infused with a sample of the patient's blood. After the last blood sample has been taken, and in order to avoid an accidental needle strike, the inner cylinder 62 is grasped, below major flange 63, and the outer sleeve 4 is moved to an axially extended position (of FIG. 8) relative to inner cylinder 62 by sliding the sleeve 64 thereover.

That is to say, equal and opposite compressive forces are applied (in the direction of the reference arrows of FIG. 7) to the outwardly extending arms 80 of locking members 78, whereby arms 80 are rotated around pivot 84 against the normal sprig bias thereof to a new position (shown in phantom) in closer proximity to outer sleeve 64. The rotation of arms 80 causes a corresponding rotation of legs 82 in an opposite direction around pivot 84 and out of proximal groove 74 to a detached position (also shown in phantom) relative to the inner cylinder 62. Accordingly, outer sleeve 64 is free to slide over inner cylinder 62 in the direction indicated by the reference arrow of FIG. 8.

After outer sleeve 64 has been axially advanced, such that the proximal end thereof is moved adjacent the distal end of inner cylinder 62, the spring biased legs 82 of locking members 78 are automatically rotated around hinges 84, through the slots 86, and snapped into receipt by the distal grooves 76 of inner cylinder 62. With the legs 82 of locking members 78 received within grooves 76, a positive, self-locking feature is established, whereby to prevent both the continued axial advancement and possible detachment of outer sleeve 64 from inner sleeve 62 as well as an inadvertent return of the outer sleeve 64 to the retracted position of FIG. 7. Therefore, a disposal cartridge is created (in FIG. 8) having the inner cylinder 62 and outer sleeve 64 locked and axially extended relative to one another with the hypodermic needle 68 completely surrounded and shielded, so as to permit the safe handling of the syringe 60 while avoiding an accidental needle strike and the possible spread of a contagious disease.

FIGS. 10-13 of the drawings show a third embodiment of the present invention for a shielded safety syringe. Like the syringes of FIGS. 1-9, the syringe 90 of FIGS. 10-13 includes an inner cylinder 92 and an outer protective sleeve 94 which are coaxially aligned and axially extensible relative to one another between a retracted position (of FIG. 10) and an axially extended position (of FIG. 11). The inner cylinder 92 has an open proximal end for receiving an evacuated phlebotomy tube (not shown) and a substantially closed distal end wall. A screw threaded hub 96, which carries a double ended needle 98, is retained within a distal bore formed through a neck 100 which extends from the distal end wall of inner cylinder 92, whereby one end of the needle 98 projects outwardly from the inner cylinder 92, and the opposite end projects into the cylinder 92 for communication with the phlebotomy tube.

The outer sleeve 94 includes an open proximal end for passing the inner cylinder 92 therethrough and a substantially closed, flanged distal end wall 101 having a hollow neck 102 extending outwardly therefrom. Neck 102 is sized to accommodate the neck 100 of inner cylinder 92, so that a tight friction fit is formed therebetween when the outer sleeve 94 is moved to a retracted position relative to inner cylinder 92. Accordingly, the distal ends of inner cylinder 92 and outer sleeve 94 can be temporarily joined at their respective necks 100 and 102 to retain syringe 90 in the retracted position and thereby permit access to the needle 98 (best shown in FIG. 10). A plurality (e.g. three) of raised locking bumps 104 are coextensively formed with and project radially inward from the outer sleeve 94. The bumps 104 are spaced around the interior of outer sleeve 94 below the open proximal end thereof. A corresponding plurality (e.g. three) of parallel aligned, longitudinally extending slots 106 (best shown in FIG. 13) are respectively formed through outer sleeve 94 between pairs of bumps 104. The slots maximize the flexibility of outer sleeve 94 for retaining the locking bumps 104 in engagement with the inner cylinder 92, as will soon be explained.

Figure 12:
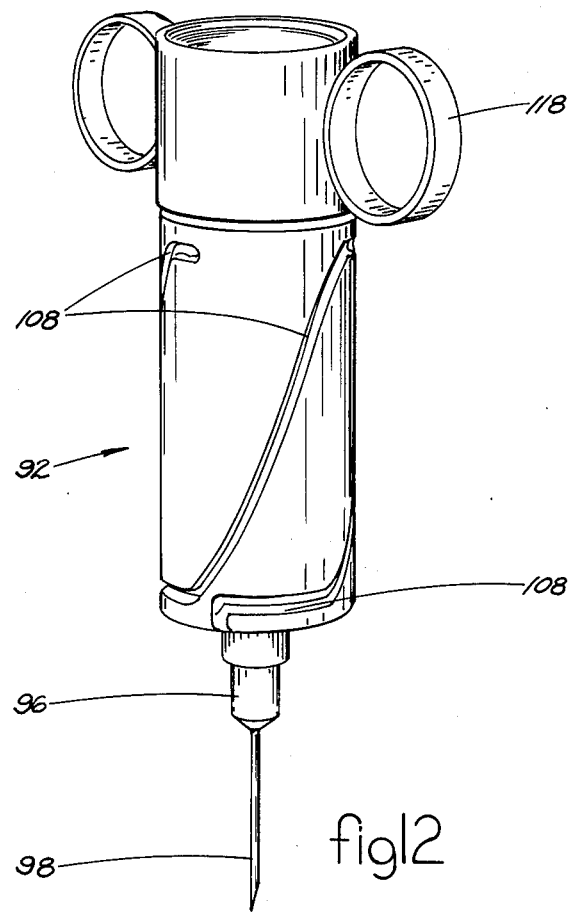
FIG. 12 is an isometric illustration of the inner cylinder of the syringe of the third embodiment.
Figure 13:
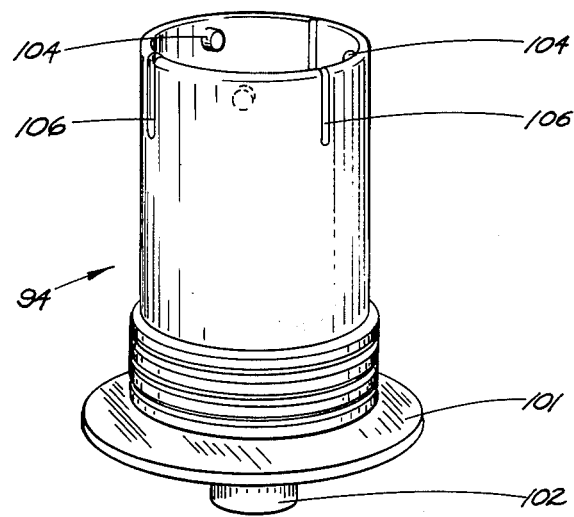
FIG. 13 is an isometric illustration of the outer sleeve of the syringe of the third embodiment.

As is best shown in FIG. 12, a series (e.g. three) of generally "S" shaped, longitudinally extending and spiraling grooves 108 are formed in the exterior of outer sleeve 94. Although an S-shaped groove is illustrated, it is to be expressly understood that grooves 108 may have any other suitable shape. The grooves 108 are spaced from one another around the periphery of outer sleeve 104 and provide guide paths through which the locking bumps 104 of inner cylinder 92 are adapted to ride when the inner cylinder 92 is moved axially between the retracted and extended positions relative to outer sleeve 94.

As is best shown in FIGS. 9 and 10, the open proximal end of inner cylinder 92 terminates at a flared portion 110. Flared portion 110 includes a slotted opening 112 extending therearound. A lip 114 is formed at the most distal aspect of flared portion 110. A cylindrical collar 116 having a pair of oppositely disposed, outwardly extending finger loops 118 and a coextensively formed, inwardly extending flange 120 is attached to the flared proximal portion 110 of inner cylinder 92. In the assembled syringe relationship shown in FIGS. 9 and 10, the flange 120 of collar 116 is received through the opening 112 in flared portion 110 and retained behind the lip 114. The lip 114 prevents the withdrawal of the flange 120 from opening 112 and the removal of collar 116 for the flared proximal portion 110 of inner cylinder 92. However, the inner cylinder 92 is free to rotate relative to both outer sleeve 94 and collar 116.

The operation of the syringe 90 is best described while continuing to refer to FIGS. 10-13. In FIG. 10, the inner cylinder 92 is located at the retracted position relative to outer sleeve 94 and the locking bumps 104 of inner cylinder 92 are positioned at the proximal ends of grooves 108. The hypodermic needle 98 is now exposed for penetrating the skin of the patient, so that a phlebotomy tube (not shown) may be infused with a sample of the patient's blood. After the last blood sample has been taken, and in order to avoid an accidental needle strike, the outer sleeve 94, below flanged end wall 101, and the finger loops 118 of the collar 116 are grasped, and the inner cylinder 92 is pulled to the axially extended position (of FIG. 11) relative to outer sleeve 94, whereby cylinder 92 is caused to simultaneously slide and rotate through sleeve 94. That is to say, the bumps 104 of outer sleeve 94 ride along the spiraling grooves 108 from the proximal to the distal ends thereof until inner cylinder 92 has been axially advanced, such that the distal end thereof is moved adjacent the proximal end of outer sleeve 94. The axial advancement of inner cylinder 92 through outer sleeve 94 and the corresponding travel of locking bumps 104 through spiraling grooves 108 causes an automatic rotation of the inner cylinder 92 relative to outer sleeve 94 and collar 116. The axial and rotational movement of inner cylinder 92, as the cylinder is moved through outer sleeve 94 to the axially extended position, is indicated by the pair of reference arrows in FIG. 11.

When the locking bumps 104 are seated at the distal ends of spiraling grooves 108, a self-locking feature is established, whereby to prevent both the continued axial advancement and possible detachment of inner cylinder 92 from outer sleeve 94 as well as an inadvertent return of inner cylinder 92 to the retracted position of FIG. 10. Therefore, a disposal cartridge is created (in FIG. 11) having the inner cylinder 92 and outer sleeve 94 axially extended and locked relative to one another with hypodermic needle 98 completely surrounded and shielded, so as to permit the safe handling of syringe 90 while avoiding an accidental needle strike and the possible spread of a contagious disease.

FIGS. 14-18 of the drawings show a fourth embodiment of the present invention for a shielded safety syringe. Like the previously described syringes of FIGS. 1-13, the syringe 130 of FIGS. 14-18 includes an inner cylinder 132 and an outer protective sleeve 134 which are coaxially aligned and axially extensible relative to one another from a retracted position (of FIG. 14) to an axially extended position (of FIG. 15). The inner cylinder 132 has an open, flanged proximal end for receiving an evacuated phlebotomy tube (not shown) and a substantially closed distal end wall 135. A screw threaded hub 136, which carries a double ended needle 138, is retained within a distal bore formed through a neck 140 which extends from the distal end wall 135 of inner cylinder 132, whereby one end of needle 138 projects outwardly from the inner cylinder 132, and the opposite end of needle 138 projects into the cylinder 132 for communication with the phlebotomy tube.

Figure 16:
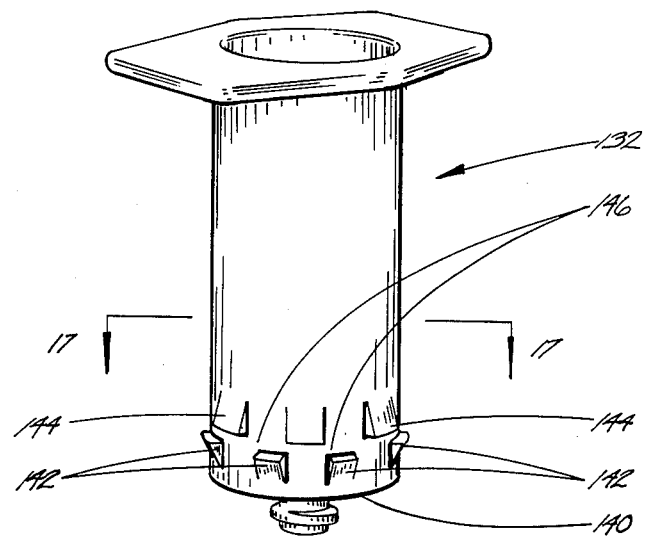
FIG. 16 is an isometric illustration of the inner cylinder of the syringe of the fourth embodiment.
Figure 17:
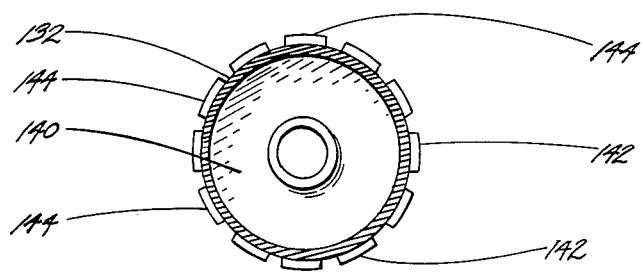
FIG. 17 is a cross-section taken along lines 17—17 of FIG. 16.
Figure 18:
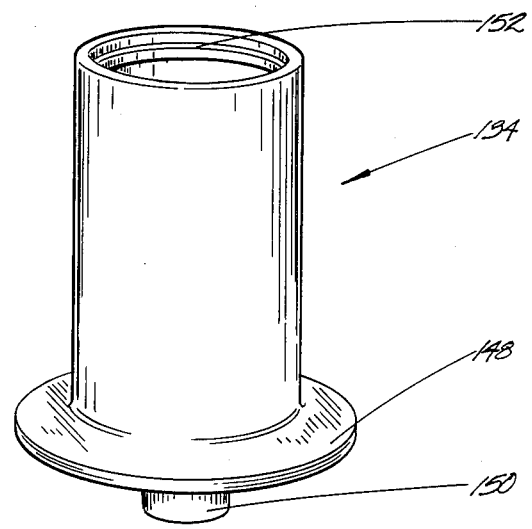
FIG. 18 is an isometric illustration of the outer sleeve of the syringe of the fourth embodiment.

Coextensively formed with and projecting outwardly from the inner cylinder 132 are first and second series of relatively short ramps 142 and 144 (best shown in FIGS. 16 and 17). A first of a series of ramps 142 extend in spaced, parallel alignment with one another around the distal end of inner cylinder 132. The second series of ramps 144 are spaced proximally from ramps 142 and also extend in spaced, parallel alignment with one another around inner cylinder 132. However, ramps 142 are interspersed between respective pairs of ramps 144. Ramps 142 slope upwardly in a proximally oriented direction, and ramps 144 slope upwardly in a distally oriented direction, such that the most elevated ends of ramps 142 and 144 oppose one another to establish a narrow, annular gap 146 in the space therebetween.

The outer sleeve 134 includes an open proximal end for passing the inner cylinder 132 therethrough and a substantially closed, flanged distal end wall 148 having a hollow neck 150 extending outwardly therefrom. The neck 150 of outer sleeve 134 is sized to accommodate the neck 140 of inner cylinder 132 therewithin. A screw thread is formed around the inside of the neck 150 of outer sleeve 134 to be mated to a corresponding screw thread formed around the neck 140 of inner cylinder 132 (best illustrated in FIG. 14). Accordingly, when the outer sleeve 134 is located in the retracted position relative to inner sleeve 132, the inner cylinder and outer sleeve may be interconnected to one another at their respective necks 140 and 150 to permit access to needle 138. An annular rim 152 (best shown in FIG. 18) is coextensively formed with and extends around the interior of outer sleeve 134 at the proximal end thereof for a purpose which will now be described.

Figure 14:
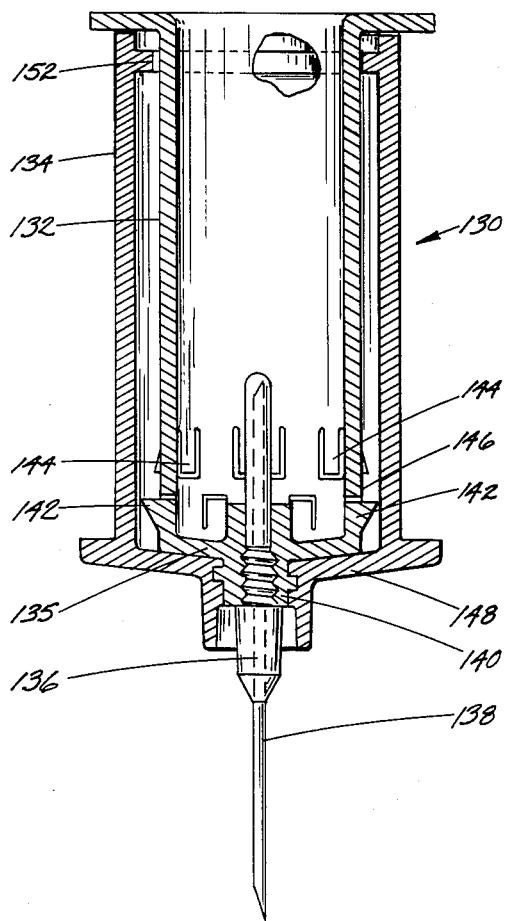
FIG. 14 shows a cross-section of the shielded syringe according to a fourth embodiment of the invention having an inner needle carrying cylinder and an outer protective sleeve locked in a retracted position relative to one another.
Figure 15:
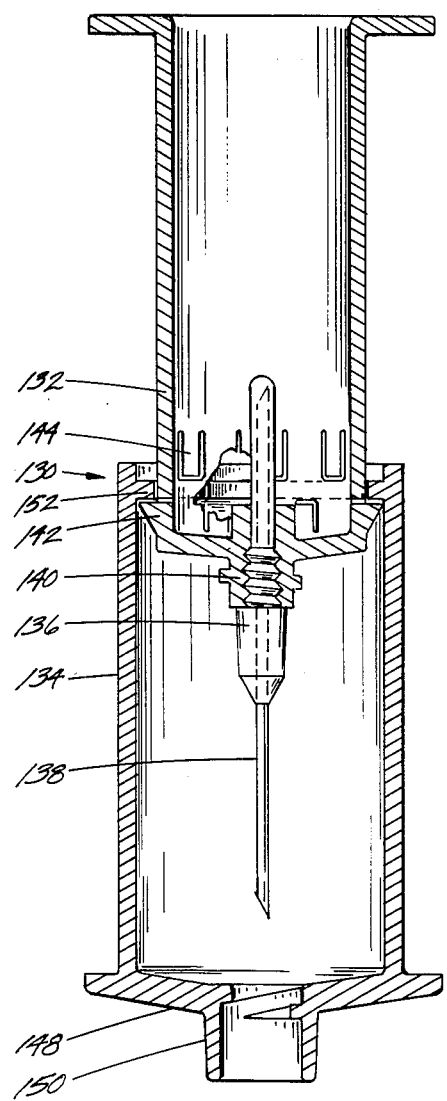
FIG. 15 shows the cross-section of the syringe of the fourth embodiment with the inner cylinder and outer sleeve axially advanced relative to one another to the extended position.

The operation of the syringe 130 is now disclosed while continuing to refer to FIGS. 14-18 of the drawings. In FIG. 14, the outer sleeve 134 is located in the retracted position relative to inner cylinder 132, such that the annular rim 152 of outer sleeve 134 is positioned proximally from and out of engagement with the ramps 142 and 144 of the inner cylinder 132. The inner cylinder and outer sleeve are connected together at their respective screw threaded necks 140 and 150, whereby to expose the hypodermic needle 138 for penetrating the skin of a patient, so that a phlebotomy tube (not shown) may be infused with a sample of the patient's blood. After the last blood sample has been taken, and in order to avoid an accidental needle strike, the outer sleeve 134 is grasped, below flanged end wall 148, and pulled to the axially extended position (of FIG. 15) relative to inner cylinder 132.

The axial advancement of outer sleeve 134 causes a corresponding advancement of the rim 152, such that rim 152 travels up and across the proximally oriented series of ramps 144. The continued axial advancement of outer sleeve 134 relative to inner cylinder 132 will cause rim 152 to be snapped into the gap 146 between ramps 142 and 144. A positive selflocking feature is thereby established, because the rim 152 of outer sleeve 134 is securely and permanently retained within the gap 146 between the most elevated portions of ramps 142 and 144. Hence, the ramps 142 and 144 form stops to prevent both the continued axial advancement and possible detachment of the outer sleeve 134 from the inner cylinder 132 as well as an inadvertent return of the outer sleeve 134 to the retracted position of FIG. 14. Therefore, a disposal cartridge is created (in FIG. 15) having the inner cylinder 132 and outer sleeve 134 locked in the axially extended position with the hypodermic needle 138 completely surrounded and shielded, so that the syringe 130 may be safely handle while avoiding an accidental needle strike and the possible spread of a contagious disease.

Figure 21:
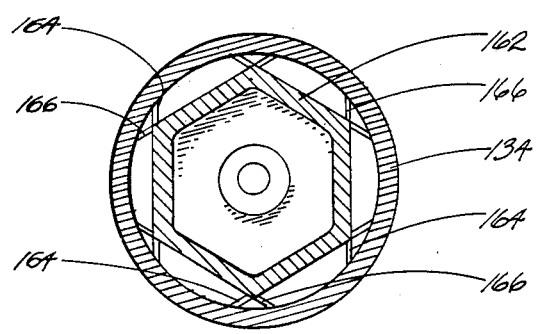
FIG. 21 is a cross-section taken along lines 21—21 of FIG. 19.
Figure 22:
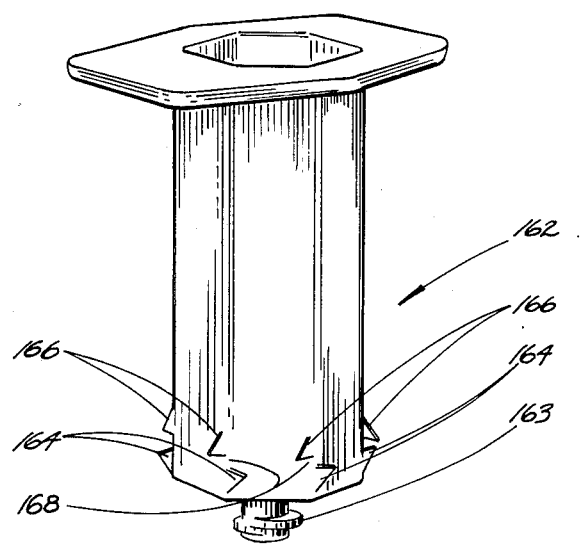
FIG. 22 is an isometric illustration of the inner cylinder of the syringe of the fifth embodiment.
Figure 23:
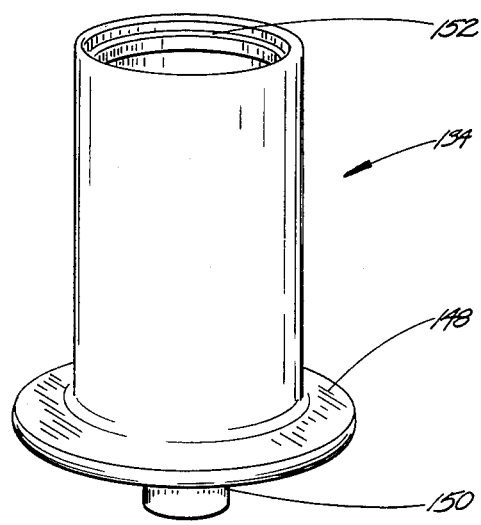
FIG. 23 is an isometric illustration of the outer sleeve of the syringe of the fifth embodiment.

FIGS. 19-23 of the drawings show a fifth embodiment of the present invention for a safety syringe. The syringe 160 of FIGS. 19-23 includes an inner cylinder and outer protective sleeve which are coaxially aligned and axially extensible relative to one another from a retracted position (of FIG. 19) to an axially extended position (of FIG. 20). As is best illustrated in FIG. 23, the outer sleeve 134 of syringe 160 is identical to the outer sleeve which was previously described when referring to the syringe 130 of FIGS. 14-18. Therefore, identical reference numerals will be used to describe the outer sleeve 134 of FIGS. 19-23, and the details thereof will be omitted. Likewise, the screw threaded hub 136 and hypodermic needle 138 of syringe 160 are identical to those of the syringe 130. Therefore, identical reference numerals will also be used to refer to hub 136 and needle 138.

As is best shown in FIG. 21, the inner cylinder 162 of the syringe 160 has a hexagonal cross-section comprising a plurality of contiguous sidewalls. Inner cylinder 162 also has an open flanged proximal end for receiving an evacuated phlebotomy tube (not shown) and a substantially closed distal end wall. The hypodermic needle carrying hub 136 is retained within a distal bore formed through a neck 163 which extends from the distal end wall of inner cylinder 162, whereby one end of needle 138 projects outwardly from the inner cylinder, and the opposite end of needle 138 projects into the cylinder for communication with the phlebotomy tube.

Coextensively formed with and projecting outwardly from the distal end of inner cylinder 162 are first and second series of short ramps 164 and 166 (best illustrated in FIG. 22). The first series of ramps 164 project outwardly in a first direction from the respective intersections of adjacent sidewalls which define hexagonal inner cylinder 162. A second series of ramps 166 are spaced proximally from ramps 164 and project outwardly in a second direction from the respective intersections of the sidewalls of inner cylinder 162. As is best shown in FIG. 21, an angle of approximately 120 degrees is formed between the first and second directions in which the first and second series of ramps 164 and 166 respectively extend from the intersections of the sidewalls of inner cylinder 162. Ramps 164 slope upwardly in a proximally oriented direction, and ramps 166 slope upwardly in a distally oriented direction, such that the most elevated ends 164 and 166 oppose one another to establish a narrow, annular gap 168 in the space therebetween.

Figure 19:
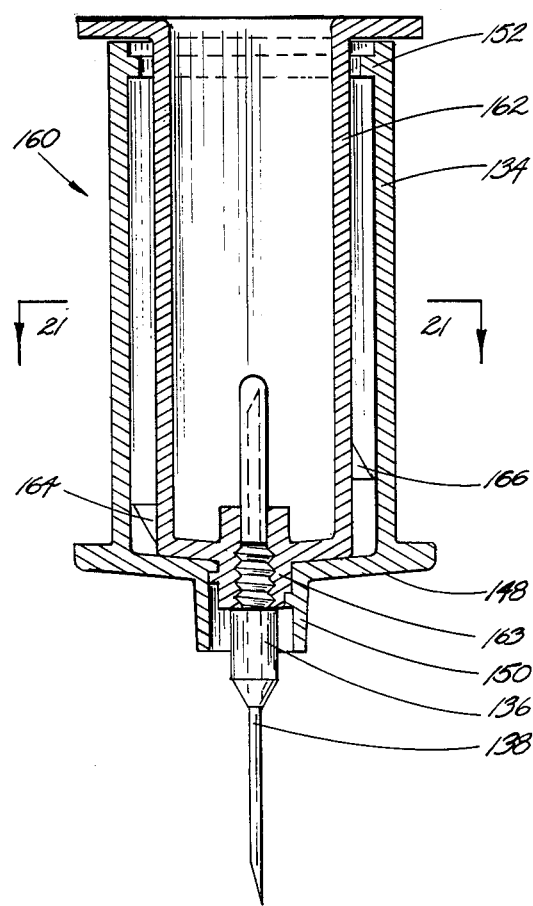
FIG. 19 shows a cross-section of the shielded syringe according to a fifth embodiment of the invention having an inner needle carrying cylinder and an outer protective sleeve locked in a retracted position relative to one another.
Figure 20:
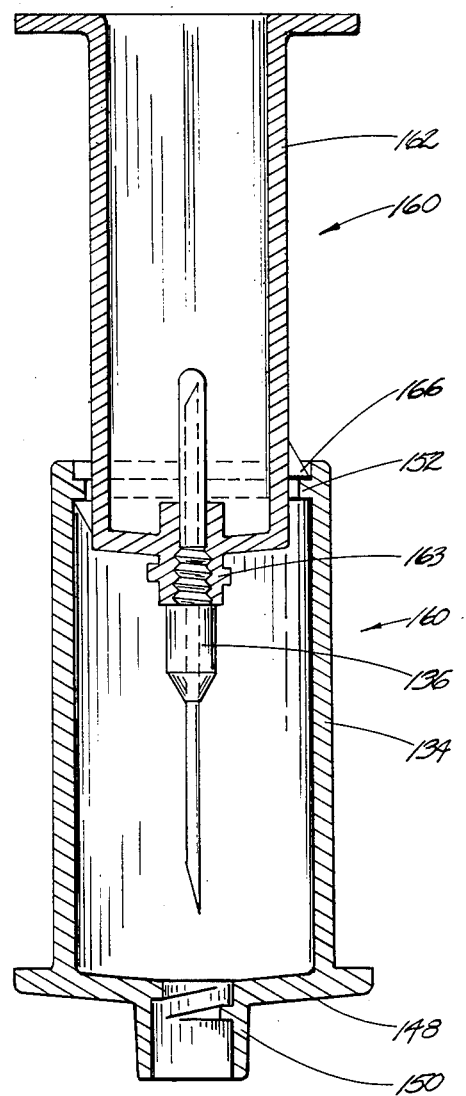
FIG. 20 shows the cross-section of the syringe of the fifth embodiment with the inner cylinder and outer sleeve axially advanced relative to one another to the extended position.

The operation of the syringe 160 is now described while continuing to refer to FIGS. 19-23 of the drawings. In FIG. 19, the outer sleeve 134 is located in the retracted position relative to inner sleeve 162, such that the annular rim 152 of outer sleeve 134 is positioned proximally from and out of engagement with the ramps 164 and 166 of the inner cylinder 162. The inner cylinder and outer sleeve are connected together at their respective screw thread necks 163 and 150, whereby to expose the hypodermic needle 138 for penetrating the skin of a patient so that a phlebotomy tube (not shown) may be infused with a sample of the patient's blood. After the last blood sample has been taken, and in order to avoid an accidental needle strike, the outer sleeve 134 is grasped, below flanged end wall 148, and a pulled to the axially extended position (of FIG. 20) relative to inner cylinder 162.

The axial advancement of outer sleeve 134 causes a corresponding advancement of the rim 152, such that rim 152 travels up and over the proximally oriented series of ramps 166. The continued axial advancement of outer sleeve 134 relative to inner cylinder 162 will cause rim 152 to be snapped into the gap 168 between ramps 164 and 166. A positive self-locking feature is thereby established, because the rim 152 of outer sleeve 134 is securely and permanently retained within the gap 168 between the most elevated portions of ramps 164 and 166. Hence, the ramps 164 and 166 form stops to prevent both the continued axial advancement and possible detachment of the outer sleeve 134 from the inner cylinder 162 as well as an inadvertent return of the outer sleeve 134 to the retracted position of FIG. 19. Therefore, a disposal cartirdge is created (in FIG. 20) having the inner cylinder 162 and outer sleeve 134 locked in the axially extended position with the hypodermic needle 138 completely surrounded and shielded, so that the syringe 160 may be safely handled while avoiding an accidental needle strike and the possible spread of a contagious disease.

It will be apparent that while preferred embodiments of the present invention has been shown and described, various modifications and changes may be made without departing from the true spirit and scope of the invention.

Having thus set forth the preferred embodiments of this invention, what is claimed is:

1. A shielded syringe assembly comprising an inner syringe cylinder having an open proximal end and a substantially closed distal end, a hypodermic needle supported at and extending outwardly form said distal end, and an outer protective sleeve having an open proximal end and an opening in a substantially closed distal end, said outer sleeve coaxially aligned with and axially advanceable relative to said inner cylinder from a retracted position, where said needle projects outwardly through the opening in said sleeve, to an extended position, where said needle is located within and completely surrounded by said sleeve;

said inner cylinder having at least one ramp and one stop spaced axially from one another; and said outer sleeve having a lip formed at the open proximal end thereof;

the continuous axial advancement of said outer sleeve from the retracted position to the extended position causing said lip to ride up the ramp of said inner cylinder and into the space between said ramp and said stop to thereby lock said outer sleeve in the extended position relative to said inner cylinder with said needle shielded by said outer sleeve.

2. The syringe recited in claim 1, wherein said hypodermic needle is double ended, such that one end thereof communicates with the interior of said inner cylinder and the opposite end extends outwardly from the distal end of said inner cylinder for penetrating the skin of a patient.

3. The syringe recited in claim 1, wherein said hypodermic needle is carried by a screw threaded hub, said hub being received within a screw threaded opening formed in the distal end of said inner cylinder, such that said needle is coaxially aligned with said inner cylinder and said outer sleeve.

4. The syringe recited in claim 1, wherein said inner cylinder has a hollow neck extending outwardly from the distal end thereof for receiving said hypodermic needle therethrough, and said outer sleeve has a hollow neck extending outwardly from the distal end thereof and surrounding the opening formed therein, the neck of said outer sleeve being sized to receive the neck of said inner cylinder therewithin when said outer sleeve is in the retracted position relative to said inner cylinder, such that said inner cylinder and said outer sleeve may be joined to one another at their respective necks.

5. The syringe recited in claim 1, wherein said inner cylinder has a series of said ramps and a series of said stops, said stops being in spaced, parallel alignment with one another and extending around the periphery of said inner cylinder at the distal end thereof, and said ramps also being in spaced, parallel alignment with one another and extending around the periphery of said inner cylinder, said series of ramps being spaced proximally from said series of stops.

6. The syringe recited in claim 5, wherein said series of ramps are arranged in an interspersed alignment with respect to said series of stops.

7. The syringe recited in claim 5, wherein each ramp of said series of ramps and each stop of said series of stops extends axially along said inner cylinder and comprises an inclined portion, said series of ramps inclining in a distally oriented direction and said series of stops inclining in a proximally oriented direction.

8. The syringe recited in claim 5, wherein said inner cylinder has a hexagonal cross-section comprising a pluraltiy of contiguous sidewalls, each ramp of said series of ramps projecting outwardly in a first direction from a respective intersection of a pair of adjacent sidewalls, and each stop from said series of stops projecting outwardly in a second direction from said respective intersection.

9. A shielded safety syringe comprising an inner cylinder having proximal and distal ends and a hypodermic needle supported by and extending outwardly from said distal end, said syringe further comprising:

an outer sleeve having proximal and distal ends and being coaxially aligned with and movable axially relative to said inner cylinder from a retracted position, where said needle projects past the distal end of said outer sleeve, to a distally advanced position, where said needle is located within and completely surrounded by said outer sleeve;

first and second locking means being axially spaced from one another and projecting from one of said inner cylinder or said outer sleeve; and third locking means projecting from the other of said inner cylinder or said outer sleeve;

the continuous axial movement of said outer sleeve from the retracted position to the distally advanced position causing said third locking means to be received in the space between said first and second locking means to thereby lock said outer sleeve at the distally advanced position with said needle shielded by said outer sleeve.

10. The syringe recited in claim 9, wherein said first locking means includes at least one ramp and said second locking means includes at least one stop.

11. The syringe recited in claim 9, wherein said first locking means includes a plurality of ramps and said second locking means includes a plurality of stops, said pluralities of ramps and stops extending around the periphery of the said one of said inner cylinder or outer sleeve.

12. The syringe recited in claim 11, wherein said pluralities of ramps and stops extend around the periphery of said inner cylinder adjacent the distal end thereof.

13. The syringe recited in claim 11, wherein said plurality of ramps are arranged in interspersed alignment with respect to said plurality of stops.

14. The syringe recited in claim 11, wherein said pluralities of ramps extend around the periphery of said inner cylinder in spaced, parallel alignment with said plurality of stops.

15. The syringe recited in claim 9, wherein said third locking means includes at least one lip.

16. The syringe recited in claim 15, wherein said lip extends around the periphery of said other of said inner cylinder or outer sleeve.

17. The syringe recited in claim 16, wherein said lip extends around the periphery of said outer sleeve adjacent the proximal end thereof.

18. The syringe recited in claim 9, wherein said first locking means includes at least one ramp and said second locking means includes at least one stop, said ramp and said stop projecting from said inner cylinder adjacent the distal end thereof; and said third locking means includes a lip projecting from said outer sleeve adjacent the proximal end thereof.

19. The syringe recited in claim 9, wherein said hypodermic needle is double ended, one end of said needle communicating with the interior of said inner cylinder and the opposite end of said needle extending outwardly from said cylinder for penetrating the skin of a patient.

20. The syringe recited in claim 9, wherein said needle is carried by a screw threaded hub located at the distal end of said inner cylinder, said outer sleeve having a screw threaded neck formed in the distal end thereof, said screw threaded hub being received within and mated to said screw threaded neck to releasably retain said outer sleeve in the retracted position with said needle projecting past the distal end of said outer sleeve.

21. A shielded safety syringe comprising an inner cylinder having proximal and distal ends and a hypodermic needle supported by and extending outwardly from said distal end, said syringe further comprising:
- an outer sleeve coaxially aligned with and movable axially relative to said inner cylinder from a retracted position, where said needle projects past said outer sleeve, to a distally advanced position, where said needle is located within and completely surrounded by said outer sleeve;
- first and second locking means being axially spaced from one another and extending around the periphery of one of said inner cylinder or said outer sleeve in parallel alignment with each other; and
- third locking means projecting from the other of said inner cylinder or said outer sleeve;
- the continuous axial movement of said outer sleeve from the retracted position to the distally advanced position causing said third locking means to be received in the space between said first and second locking means to thereby lock said outer sleeve at the distally advanced position with said needle shielded by said outer sleeve.

* * * * *